United States Patent [19]

Geary, Sr.

[11] Patent Number: 5,124,061
[45] Date of Patent: Jun. 23, 1992

[54] SYSTEMIC PLANT CRYOPROTECTION WITH CHOLINE SALTS

[76] Inventor: Robert J. Geary, Sr., P.O. Box 1089, 2326 Atlantic Blvd., Vero Beach, Fla. 32960

[21] Appl. No.: 678,056

[22] Filed: Apr. 1, 1991

[51] Int. Cl.$^5$ .............................................. C09K 3/18
[52] U.S. Cl. .......................................... 252/70; 47/2; 106/13; 564/293
[58] Field of Search .............. 106/13; 47/2; 252/70, 252/546, 547, 548, 174.21; 260/404; 560/253; 562/606, 607; 564/293

[56] References Cited

U.S. PATENT DOCUMENTS 4,461,716 7/1984 Barbarin et al. .................... 47/2
4,618,442 10/1986 Geary et al. ..................... 252/70

FOREIGN PATENT DOCUMENTS 57-162798 10/1982 Japan .

Primary Examiner—A. Lionel Clingman
Assistant Examiner—Christine A. Skane
Attorney, Agent, or Firm—Samson B. Leavitt; Michael A. Leavitt

[57] ABSTRACT

A method of increasing the resistance of plants to damage by freezing conditions by treating the plants, prior to exposure to such conditions, to or with a composition containing a choline salt of a monocarboxylic or polycarboxylic acid which is absorbed into the plant vascular system where it exerts it cryoprotective effects. Aqueous and powder compositions containing the choline salt combined with glycerin, propylene glycol and/or a water soluble nonionic surface active polyethoxylated polyoxpropylene block copolymer.

17 Claims, No Drawings

SYSTEMIC PLANT CRYOPROTECTION WITH CHOLINE SALTS

This invention relates to compositions, methods and apparatus for plant cryoprotection, i.e., for increasing the resistance of plants to damage by low, especially freezing, temperatures.

Freezing temperatures have always been a major cause of temporary or permanent damage to plants and plant parts including seedings, shoots, trunks, bark, growing points, buds, leaves, flowers, fruits and/or vegetables.

Some plants, notably those of the crucifer family, and many others have the built in ability to withstand low temperatures for many hours, but many plants, especially citrus plants, are highly sensitive to even slight exposure to freezing conditions. The agricultural areas of the world have been periodically devastated by unexpected and severe freezes. As an example, in the state of Florida, at different intervals, freezing of citrus trees has resulted in the loss of millions of dollars. In 1981 and 1985, large areas of Florida that normally were citrus producing areas, were wiped out. The farmers of these areas have been hesitant to replant because freezing comes regularly. At one time citrus crops were produced as far north as Jacksonville, Fla., but at present no citrus crops are grown in these areas except a few varieties such as the Mandarin tangerine type.

Numerous types of approaches have been devised for the purpose of inhibiting such plant damage, including laborious, time-consuming and costly development of hardy plant species, mechanical protection such as coating and bagging, and the like. Accepted methods of frost control using wind machines, heaters and/or irrigation involve a high capital cost followed by increasing running costs of rising fuel prices. Treatment, e.g. spraying, of the plant with a suitable cryoprotectant chemical prior to exposure to freezing conditions would appear to constitute a simple and relatively inexpensive solution to this problem. Plant growth inhibitors and other chemicals which delay growth and/or bud development in the spring and thereby avoid injury caused by spring freezes have generally been found to introduce side effects and/or reduce crop yields. Other types of chemicals have been experimented with for plant cryoprotection including polyvinyl pyrrolidone, glycerol, ethylene glycol, and the dodecyl ether of polyethylene glycol (DEPEG). However, as stated in "Analysis and Improvement of Plant Cold Hardness" by Olien and Smith, CRC Press, Inc., Boca Raton, Fla. (1981), page 188, "Despite numerous attempts to increase hardiness with chemicals, few if any practical applications have resulted to date... The search for chemicals which will increase hardiness continues, however, and may well lead to commercially acceptable methods of reducing field injury."

U.S. Pat. No. 4,618,442 issued Oct. 21, 1986 to Robert J. Geary III and the present applicant, discloses and claims cryoprotectant methods and compositions employing as the essential active cryoprotectant component a water soluble nonionic surface active polyethoxylated polyoxypropylene block copolymer having a molecular weight (M.W.) of about 2,000 to about 7,000 and a molar ratio of propylene oxide to ethylene oxide of about 2.5:1 to about 7:1.

It is an object of this invention to provide still another effective cryoprotectant chemical. Another object of this invention is the provision of a plant cryoprotectant chemical which will not be subject to one or more of the above disadvantages. Still another object of this invention is the provision of a plant cryoprotectant chemical which is nonphytotoxic, non-toxic, biodegradable and environmentally acceptable. Yet another object of this invention is the provision of compositions and methods for employing such chemical for cryoprotection, i.e. increasing the resistance of plants to damage by low, especially freezing, temperatures. Other objects and advantages will appear as the description proceeds.

According to certain of its aspects, the attainment of one or more of the above objects is made possible by this invention which includes a method of increasing the resistance of plants to damage by freezing conditions comprising applying to the plants prior to exposure to such conditions an effective cryoprotectant amount of a composition containing an effective amount, as an essential cryoprotectant component, of a salt (e.g. reaction product) of choline with a monocarboxylic or polycarboxylic acid, preferably such an acid which is aliphatic and contains about 2 to about 20 carbon atoms. The aforesaid composition can also desirably contain one or both of A. about 0.1% to about 15% of glycerin, and B. about 0.01% to about 2.5% of a water soluble nonionic surface active polyoxyethylenated polyoxypropylene block copolymer having a molecular weight of about 2,000 to about 7,000, preferably about 4,000 to about 5,000 and a molar ratio of propylene oxide: ethylene oxide (Pr. O.: E.O.) of about 2.5:1 to about 0.7:1, preferably about 1:1.

For treating the plant parts above ground, as by sprinkling or spraying, aqueous compositions, e.g. solutions, colloidal and stable dispersions and emulsions, etc., are preferred containing about 0.01% to about 2.5% of the choline salt, preferably at a pH of about 4 to about 7.5.

The invention also includes the compositions employed in the above defined method of this invention.

Choline is well known, especially in the human pharmaceutical field. Chemically, it is N-hydroxyethyl-N, N, N-trimethyl ammonium hydroxide, and is widely commerically available in the form of a 45% solution in methanol. It is also very soluble in ethanol and water, being per se a viscid, strongly alkaline liquid.

Any natural or synthetic, saturated or unsaturated aliphatic, aromatic or heterocyclic monocarboxylic or polycarboxylic acid may be employed to form the choline salt. The polycarboxylic acid may contain 2 up to 6 or more carboxylic groups, and at least, one, some, or all carboxylic acid groups may each be combined with the N-bound OH group of a choline molecule to form a salt containing, correspondingly, one or more choline moieties. The acids may contain inert, non-phytotoxic substituents such as alkyl, amino and hydroxyl.

Aliphatic acids of about 2 to about 20, preferably about 6 to 20, carbon atoms are preferred which may be saturated or unsaturated. Examples of saturated aliphatic mono- and poly- carboxylic acids include acetic, hexanoic, decanoic, stearic, citric, succinic, aspartic, and EDTA (ethylenediamine tetra acetic) acids and the like. Examples of unsaturated carboxylic acids include octenic, undecylenic, linolinic, linoleic and oleic acids, including the carboxylic acids in cottonseed, flax seed, safflower, corn, olive, linseed, perilla seed, tung, and soybean oils and the like.

The desired choline salts are prepared readily and in known manner by simply mixing, if desired with heating, the carboxylic acid or oil containing same with the molar amount of choline desired to form a salt with one, some or all the carboxylic groups in the carboxylic acid or oil. The reaction or salt formation may be conducted neat or in a suitable, preferably neutral solvent, inorganic or organic, including water, methanol, ethanol, isopropanol, acetone or the like. When a plant oil containing triglycerides is employed, such as the above-mentioned oils, a product results containing the choline salts of the fatty acids in the oils together with simultaneously released glycerine, which product may be employed as is in carrying out the present invention or after removal of some of the glycerine.

According to a further aspect of the invention, the compositions may contain about 0.1% to about 15% of glycerin which acts as a penetrating agent, especially with older plants containing waxy surfaces on the leaves, to assist the choline salt in penetrating the plant (including seeds) and exerting its desired cryoprotectant function systemically.

When the choline salts employed herein are insufficiently soluble or dispersible in water, another feature of the present invention comprises including in the composition a wetting, dispersing agent, especially the aforementioned nonionic polyoxyethylenated polyoxypropylene block copolymer which is a well known type of nonionic surfactant commonly made by condensing the requisite number of water solubilizing moles of ethylene oxide (E.O.) with a polypropyleneglycol hydrophobe nucleus of requisite molecular weight. These surfactants have good wetting, dispersing, emulsifying, and detergency properties combined with low foam. They have been used as detergent-active agents, and in agriculture for improving wetting properties and for solubilizing, dispersing or emulsifying other functionally active components such as pesticides, growth regulators, fertilizers and the like, i.e. as secondary, assistant or auxiliary agents and not as the sole or major active component. For any given polyoxypropylene hydrophobe, the water solubility of the copolymer varies directly with the percentage of polyoxyethylene combined therewith, i.e. the molar ratio E.O.:Pr.O., or inversely with the molar ratio Pr.O.:E.O. All the copolymers operative herein are water soluble at the defined concentrations at ambient temperatures to yield generally clear solutions, although it will be understood that the terms "water soluble", and "solution" as employed herein include products which are colloidal, or readily water-dispersible or -emulsifiable and the resulting aqueous "solutions" containing them.

The nonionic surfactant copolymers suitable for use in this invention are commercially available. The Monolan products of Diamond Shamrock Corporation, described in its Product Bulletin entitled "Monolan Series", 1982 are representative, ranging from clear liquids to pastes or semi-solids with increasing molecular weight. Preferred among such products are Monolan 2800, a clear liquid with a molecular weight (MW) of about 2800 based on a 1750 MW polyoxpropylene hydrophobe (Pr.O.:E.O. of 1.67:1); and Monolan 6400, a semi-solid of about 5800 MW based on a 3200 MW Pr.O. hydrophobe (Pr.O.:E.O. of 1.22:1). Most preferred is Monolan 4500, a semi-solid of about 4600 MW based on a 2200 MW Pr.O. hydrophobe (Pr.O.:E.O. of about 0.92:1 or about 1:1). Nonionic surfactant copolymers operative herein are also available as Pluronic products of BASF-Wyandotte.

In some applications of this invention, a powder may be provided containing the defined choline salt admixed with a solid particulate solid, which may be absorbent or adhesive, such as vermiculite, activated carbon, lime, limestone, clays, zinc oxide, magnesium oxide and the like. Such powders can generally contain about 1% to about 50% of the defined choline salt and are particularly effective for treating plant seeds. Another method of treating seeds comprises treating them with methylcellulose, carboymethyl cellulose, natural or synthetic gums, Pluronics or other sticky binders and then applying a powder containing for example about 1% to about 5% of the choline salt, with or without glycerin and/or the above defined nonionic block copolymer.

According to this invention, protection to the leaves of the plant of citrus can be attained down to about 6 degrees C below freezing point by spraying the leaves or other plant parts and-or abundantly root watering the plants with the present choline salt compositions which are absorbed by the roots and other plant parts and travel via the vascular system of the plant to the upper most branches and leaves. An important point is that in citrus at least, these choline salts prevent the bark or the skin of the tree (especially young saplings up to 2" in diameter) from burtsing or cracking under low temperatures. Such bursting or cracking presages the ultimate death of the whole tree. In experiments according to the invention, trees watered and/or sprayed at ambient temperatures with these choline salts from 2 hours to about 15 days before a freeze have resulted in excellent survival of the trees.

Orange plants of various types that are now produced for juice growing in pots were put into special chambers where the humidity and temperature of the air were measured. The temperature of the soil and the bark, and if fruit was present the fruit and inside of the fruit, were also measured. They were put in at a temperature of 35° C. and the temperature dropped at the rate of 3° C. per hour until a temperature of $-6°$ C. was reached. The plants were maintained at this temperaute for 2 hours. As an average the plants were exposed to temperatures below the freezing point for 6 to 12 hours. The result was that the controls that were untreated with choline salts, only with water, were completely destroyed (bark burst, trees died). The trees treated with the choline salts herein described lost their leaves and gave all the appearance of having been scorched by heavy freezing. However, after 2 weeks time, the plants resumed growth by bursting out with new shoots and have continued to grow in a normal manner since that time.

In the case of heavy freezing conditions, the best combination is both root-watering and spraying the plants. The plants are often permitted a minimum of 12 hours between treatment and freezing in controlled temperature chambers. It is often preferably in the tesing and use of these choline salt compositions, to permit as mush as 1 week or 10 days between the treatment and the exposure to freezing temperature. The purpose of this is to permit material to penetrate the membranes of the plants and thereby give protection to the cells of the plants. A repeat treatment at least 12 hours before freeze is needed where $-6°$ C. temperature are encountered.

Another procedure used in testing involves the use of these choline salt compositions on the blossoms or flowers of fruiting trees and plants. The fruiting plants may be peaches, apples, pears, blueberries, strawberries, citrus flowers of oranges, grapefruit or lemons or any other plant that are susceptible to the freezing of the flowers. The freezing of the flowers results in a lack of frutation of the plant so that, in many cases fruits are lost completely. In this test procedure, the flowers are put into a cool shaded room of not more than 50° F. for several hours to acclimate them to the change in temperature from the hot sunlight in which they are growing. The blossoms may be in the form of buds on small twigs or large branches of the various trees or in the case of strawberries or other low growing plants the complete plant if small, is put into the treatment. After they have been cooled from the hot sunlight to 80° F. or less, they are sprayed with the selected choline salts to be tested. The spraying is done with a small air propelled spray. After spraying, they are permitted to dry for 2 to 3 hours or if they are plants growing in pots, they are merely exposed after the spraying to the temperature of the room which should be relatively cool, less than 80° F. After a period of 3 hours permitting the absorption of the compounds into the blossoms, twigs, branches, etc., they are put into a freezing chamber starting at 40° F., and the temperature dropped gradually to −26° F. After they have reached the temperature of −26° F. they are kept there for a minimum of 2 hours after which they are removed and put into a room at not more than 70° F. Immediately after this treatment, they appear to have been hurt as by blow torch. However, after a day or two they recover and are again able to produce fruit.

Although the compositions of this invention may be applied to the plants immediately prior to exposure to freezing conditions to obtain cryoprotective results, it is often preferred for optimal results to apply the solutions at least about 6 hours, preferably at least about 24 hours, prior to such exposure to permit more complete absorption of the solutions. For similar reasons, the treated portions of the plants should not be watered or sprayed with any other liquid medium for at least about 6 hours, preferably at least about 24 hours, following the treatment. Any such inadvertent watering or spraying, or rain, during such initial period of absorption may necessitate repetition of the choline salt treatment of this invention. The cryoprotective effects are retained up to about 30 days or more after treatment with these compositions, as evidenced by significant reductions in bark and stem splitting, defoliation, foliage burn, fruit damage or drop yellowing, dessication, and other plant damage and mortality when the treated plants are subjected to freezing conditions.

Any suitable plant spray apparatus suitable for spraying aqueous solutions may be employed. An example of such apparatus is a compressed air atomizer such as the Chromist Spray Unit of Gelman Instrument. The plants to be treated are lightly but thoroughly sprayed, preferably on all their surfaces, short of "run-off". The plants may be in any of their various forms, e.g. seedings, schrubs, bushes, vines, and trees in any stage of growth, and the application may be made day or night, at ambient warm room or cold temperatures.

The following examples of certain embodiments of the invention are to be regarded as only illustrative and not limitative. All amounts and proportions referred to herein and in the appended claims are by weight and temperatures are in degrees F. unless otherwise indicated.

EXAMPLE 1

18½ grams of undecylenic acid, 99% pure was reacted in a 1:1 molar ratio with 32 cc. of 45% choline in methanol for 24 hrs. at 35° C. Methanol was evaporated off to give amorphous thick jelly or monocholine undecylenate. One gram of this (105A) jelly was dissolved in osmosis purified water (300 cc.). Corn seedings were watered with 10 cc. of it to 5 inch pot. Seedlings were 10 inches tall. Frozen 7 days later, and again refrozen after another 9 days. Corn survived both freezings and continued to grow well.

EXAMPLE 2

1 gram of 105A (as in Example 1) was mixed with 300 cc. of osmosis purified water, 1 gram of a mixture of 50% Pluronic 85 and 50% propylene glycol were added and emulsified by strong agitation. pH 5. This was sprayed on corn seedlings eight inches tall, and also 10 cc. were applied to 5 inch pots of corn seedlings eight inches tall. After 7 days, the plants were exposed to temperatures starting at 40° F., and dropped gradually to 24° F. where they were held for 2 hrs. After removal from freezer, they were put into subdued light. No visible damage to any of the plants. After 10 days of continued growth, they were frozen as before. No visible damage and plants continue to grow well.

To reduce irritation to the eyes, a magnesium salt was made, using 1 mole magnesium oxide, and 2 moles of the 105A. The resulting compound was practically insoluble in water, but gradually solubilized in weak carbonated water. Zinc and iron salts were also made and tested.

EXAMPLE 3

3 moles of choline, as a 45% solution in methanol were reacted with one mole citric acid. 1 gram of the mixture so formed was dissolved in 300 cc of osmosis purified water and corn seedlings 5 inches high in 3 inch pots were watered with 5 cc of the mixture. They were frozen and refrozen as in Example 1. Results were similarly excellent.

EXAMPLE 4

4 moles of choline dissolved in methanol, 45% solution, was reacted with 1 mole of commercially available BZ acid (Ethylene Diamine tetra acetic acid). Water solution of reaction was pH 7-7.5 (essentially neutral). A mixture was made of 10 g. of 1/3 P85 Pluronic, 1/3 L 61 Pluronic, 1/3 Propylene glycol with 4 grams of the reaction product of choline and BZ acid (tetracholine ethylenediamine diacetate). One gram of this mixture was dissolved in 300 cc of osmosis purified water, and corn plants, tomato and string bean plants in 3" pots and 5 inches high were sprayed and watered (10 cc. per pot). Results were good.

EXAMPLE 5

One mole of choline as a 45% methanol solution was reacted with slightly more than one mole of glacial acetic acid to give a pH 7.5 10 gr. of the Pluronic/propylene glycol mixture of Example 4 were mixed in 300 cc. of water with 2 grams of the choline-acetic acid salt. Tomato seedlings in plant tubes sprayed with ½ to ¼ strength of the 1/300 mixture gave good results when frozen.

EXAMPLE 6

One mole of Aspartic acid, was reacted with one mole of choline as a 45% solution in methanol to give pH 4.5. 10 grams of the Pluronic/propylene glycol of Example 4 was mixed with 14 grams of the reaction product of aspartic acid and choline. One gram of the resulting mixture was dissolved in 300 cc of osmosis purified water, sprayed on bean and tomato seedlings in 3 inch pots, 15 cc. per pot, and frozen 4 days later. Results were excellent.

EXAMPLE 7

One mole choline as 45% methanol solution was reacted with one mole succinic acid. 11 grams of the reaction product was mixed with 10 g. of the Pluronic/propylene glycol mixture of Example 4. One gram of this mixture was mixed with 300 cc osmosis purified water, applied to corn seedlings 10 inches high in 5 inch pots, 10 cc to pot, frozen 16 days later, results very good. Refrozen 4 days later, very good results.

This invention has been disclosed with respect to preferred embodiments, and it will be understood that various modifications and variations thereof obvious to those skilled in the art are are to be included within the spirit and purview of this application and the scope of the appended claims.

What is claimed is:

1. A method of increasing the resistance of plants to damage by freezing conditions comprising applying to the plant at ambient non-freezing temperatures an effective cryoprotectant amount of an aqueous composition in the form of a solution, dispersion or emulsion containing about 0.1% to about 2.5%, as an essential absorbable systemic cryoprotectant component, of a salt of choline with a monocarboxylic or polycarboxylic acid about 2 hours to about 15 days prior to exposure to such freezing conditions to permit said choline salt to be absorbed into and travel through the vascular system of the plant prior to such exposure.

2. A method according to claim 1 wherein said composition further contains about 0.1% to about 15% of glycerin.

3. A method according to claim 1 wherein said composition further contains about 0.01% to about 2.5% of one or a mixture of water soluble nonionic surface active polyethoxylated polyoxpropylene block copolymers having a molecular weight of about 2,000 to about 7,000 and a molar ratio of propylene oxide:ethylene oxide of about 2.5:1 to about 0.7:1.

4. A method according to claim 3 wherein said composition further contains about 0.1% to about 15% of glycerin.

5. A method according to claim 1 wherein said composition contains a salt of choline with an aliphatic monocarboxylic or polycarboxylic acid containing about 2 to about 20 carbon atoms.

6. A method according to claim 5 wherein said composition further contains about 0.1% to about 15% of glycerin.

7. A method according to claim 5 wherein said composition further contains about 0.01% to about 2.5% of one or a mixture of water soluble nonionic surface active polyethoxylated polyoxypropylene block copolymers having a molecular weight of about 2,000 to about 7,000 and a molar ratio of propylene oxide:ethylene oxide of about 2.5:1 to about 0.7:1.

8. A method according to claim 7 wherein said composition further contains 0.5 to 1 part of propylene glycol per part of said block copolymers.

9. A method according to claim 1 wherein said cryoprotectant component comprises choline aspartate, choline undecylenate or monocholine succinate.

10. A plant cryoprotectant aqueous composition containing, approximately be weight and as essential cryoprotectant components, 0.01% to 2.5% of a salt of choline with a monocarboxylic or polycarboxylic acid, and 0.1% to 15% of glycerin.

11. A plant cryoprotectant aqueous composition containing, approximately be weight and as essential cryoprotectant components, 0.01% to 2.5% of a salt of choline with a monocarboxylic or polycarboxylic acid, and 0.01% to 2.5% of one or a mixture of water soluble nonionic surface active polyethoxylated polyoxypropylene block copolymers having a molecular weight of about 2,000 to about 7,000 and a molar ratio of propylene oxide:ethylene oxide of about 2.5:1 to about 0.7:1.

12. A composition according to claim 10 in which the monocarboxylic or polycarboxylic acid is aliphatic and contains about 2 to about 20 carbon atoms.

13. A composition according to claim 11 in which the monocarboxylic or polycarboxylic acid is aliphatic and contains about 2 to about 20 carbon atoms.

14. A composition according to claim 10 wherein said acid is selected from the group consisting of aspartic acid, undecylenic acid and succinic acid.

15. A composition according to claim 11 wherein said acid is selected from the group consisting of aspartic acid, undecylenic acid and succinic acid.

16. A composition according to claim 15 further containing about 0.5 to about 1 part of propylene glycol per part of said block copolymers.

17. A method of increasing the resistance of plants to damage by freezing conditions comprising applying to the plant seeds at least about 2 hours prior to exposure to such freezing conditions an effective cryoprotectant amount of a solid particulate composition containing about 0.01% to about 50% of a salt of choline with an aliphatic monocarboxylic or polycarboxylic acid containing about 2 to about 20 carbon atoms.

* * * * *